(12) United States Patent
Majeed et al.

(10) Patent No.: US 10,588,844 B2
(45) Date of Patent: Mar. 17, 2020

(54) PROCESS FOR PREPARING TRIPEPTIDE CONTAINING OLEANOLIC ACID AND ITS THERAPEUTIC APPLICATIONS THEREOF

(71) Applicants: Muhammed Majeed, Edison, NJ (US); Kalyanam Nagabhushanam, East Windsor, NJ (US); Lakshmi Mundkur, Bangalore (IN); Rajendran Ramanujam, Bangalore (IN)

(72) Inventors: Muhammed Majeed, Edison, NJ (US); Kalyanam Nagabhushanam, East Windsor, NJ (US); Lakshmi Mundkur, Bangalore (IN); Rajendran Ramanujam, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 0 days.

(21) Appl. No.: 16/135,240

(22) Filed: Sep. 19, 2018

(65) Prior Publication Data

US 2019/0083378 A1   Mar. 21, 2019

(30) Foreign Application Priority Data

Sep. 21, 2017 (IN) .............. 201741033476

(51) Int. Cl.
  *A61K 8/64*   (2006.01)
  *A61Q 19/08*  (2006.01)
(52) U.S. Cl.
  CPC .............. *A61K 8/645* (2013.01); *A61Q 19/08* (2013.01); *A61K 2800/56* (2013.01); *A61K 2800/57* (2013.01)

(58) Field of Classification Search
  CPC ............ A61K 2800/56; A61K 2800/57; A61K 8/645; A61Q 19/08
  See application file for complete search history.

(56) References Cited

U.S. PATENT DOCUMENTS

| | | | | |
|---|---|---|---|---|
| 8,383,594 | B2* | 2/2013 | Majeed | A61K 8/64 514/18.6 |
| 8,420,778 | B2* | 4/2013 | Ziegler | A61K 8/64 530/331 |
| 8,987,212 | B2* | 3/2015 | Majeed | A61K 8/64 514/21.8 |
| 10,071,043 | B2* | 9/2018 | Nagabhushanam | A61K 8/64 |
| 2018/0344627 | A1* | 12/2018 | Majeed | A61Q 17/04 |
| 2018/0344628 | A1* | 12/2018 | Majeed | A61K 8/99 |
| 2019/0060216 | A1* | 2/2019 | Majeed | A61Q 17/00 |

FOREIGN PATENT DOCUMENTS

DE   102005063179   *   9/2006   ............. A61K 45/06

OTHER PUBLICATIONS

DE102005063179, published Sep. 2006, translation to English accessed online at https://patents.google.com/patent/DE102005063179A1/en?oq=102005063179 on Aug. 2, 2019. 34 pages. (Year: 2006).*
Guzman et al. Peptide synthesis: chemical or enzymatic. Electronic Journal of Biotechnology, vol. 10 No. 2, pp. 279-314. (Year: 2007).*

* cited by examiner

*Primary Examiner* — Marcela M Cordero Garcia

(57) ABSTRACT

The present disclosure provides oleanoyl tripeptide to prevent skin aging. More specifically the invention discloses the anti-collagenase, anti-elastase, enhancement of TGF-β secretion in fibroblasts, UV protection, oxidative stress protection, and other properties of the oleanoyl-KVK tripeptide which aids in preventing skin aging.

15 Claims, 11 Drawing Sheets

ANNEXIN

Oleanoyl KVK – 12.5 µg/ml

PROCESS FOR PREPARING TRIPEPTIDE CONTAINING OLEANOLIC ACID AND ITS THERAPEUTIC APPLICATIONS THEREOF

CROSS REFERENCE TO RELATED APPLICATION

This is a conventional US patent application claiming priority from Indian Provisional application no. 201741033476 filed on 21 Sep. 2017, the details of which are being incorporated herein by reference.

FIELD OF THE INVENTION

The present invention relates to anti-aging skin care tripeptide. In particular the present invention relates to a process for preparing tripeptide containing oleanolic acid and its therapeutic applications.

DESCRIPTION OF PRIOR ART

Skin is the largest and most massive organ of the human body. Human skin consists of the outermost epidermal layer and the dermis consists of vascular connective tissue below the epidermis. The epidermis is primarily composed of keratinocytes, which produce keratins, intermediate filaments that provide mechanical stability. The dermis is largely composed of dense collagen rich extracellular matrix (ECM). ECM is synthesized, organized, and maintained by dermal fibroblasts which are responsible for the skin's tensile strength and mechanical properties.

With increase in age, the human skin is subjected to many changes which include collagen and elastin breakdown, sagging, wrinkles, thinning of epidermis, decrease in melanocyte and loss of melanin production, sebaceous glands produce less oil leading to loss of moisture and dryness, loss of subcutaneous fat layer, loss of insulation and padding and weak wound healing ability. There are several factors that cause premature skin aging and can be influenced to introduce graceful skin aging.

Peptides are involved in many physiological processes. Peptides in cosmetic products are known to slow down or reverse aging. There are different classes of peptides which include: signaling peptides, enzyme inhibitor peptides, neurotransmitter-affecting peptides, carrier peptides etc.

Prevention of skin aging is now being targeted widely by the industry players in the field of cosmetics and there is requirement for products that prevent skin aging. Synthetic peptides are now being used in the skin care industry due to the benefits they provide. The role of synthetic peptides in aging, beauty, photo damage, and skin health are well described in the following prior art documents:

U.S. Pat. No. 6,620,419B1 relates to cosmetic or dermopharmaceutical use of peptides for healing, hydrating and improving skin appearance during natural or induced ageing (heliodermia, pollution).

US20130336904A1 relates to novel anti-ageing peptides modulating surviving and compositions including same.

US20110160137A1 relates to composition containing collagen peptide for improving skin care.

Though the use of synthetic peptides for use in skin care is known but a tripeptide: Lysine-Valine-Lysine (KVK) conjugated to Oleanolic acid is not known in the art. Further the synthetic peptides which are in use nowadays for skin care are expensive. Hence there exist a need to design a synthetic peptide which is cheaper and can be used effectively to reduce all signs of aging. The present invention solves the above mentioned problem by disclosing the beneficial effects of the a tripeptide: Lysine-Valine-Lysine (KVK) conjugated to Oleanolic acid on reducing skin aging.

It is the principle objective of the invention to disclose a process for preparing a tripeptide containing oleanolic acid having anti skin aging properties.

Another objective of the instant invention is to disclose the anti aging activity of the tripeptide Lysine-Valine-Lysine (KVK) conjugated to Oleanolic acid by being an anti-inflammatory agent and inhibiting the activities of collagenase and elastase.

The present invention fulfills the above mentioned objectives and further related advantages.

SUMMARY OF THE INVENTION

The present invention discloses oleanoyl-KVK tripeptide to prevent skin aging. More specifically the invention discloses the anti-collagenase, anti-elastase, UV protection, oxidative stress protection, and other properties of the oleanoyl-KVK tripeptide which aids in preventing skin aging and thus an important skin care product.

In an aspect of the present invention, there is provided a process for preparing tripeptide of structure 1 and SEQ ID 1 attached to oleanolic acid comprising the steps of: (a) Treating Boc-Lys(Cbz)-OH, wherein both the amino acid groups of L-Lysine is protected, with Benzyl bromide in Acetone and potassium carbonate to get Boc-Lys(Cbz)-OBzl; (b) Hydrolyzing the Boc-Lys(Cbz)-OBzl from step (a) to obtain H-Lys(Cbz)-OBzl-HCl; (c) Coupling the H-Lys(Cbz)-OBzl-HCl of step (b) with Boc-Val-OH in the presence of N, N'-Dicyclohexylcarbodiimide, Hydroxy benzotriazole and triethylamine to obtain Boc-Val-Lys(Cbz)-OBzl; (d) Treating Boc-Val-Lys(Cbz)-OBzl obtained from step (c) with trifluoroacetic acid to obtain H-Val-Lys(Cbz)-OBzl; (e) Coupling H-Val-Lys(Cbz)-OBzl of step (d) with Boc-Lys(Cbz)-OH in the presence of N, N'-Dicyclohexylcarbodiimide, Hydroxy benzotriazole and triethylamine to obtain Boc-Lys(Bzl)-Val-Lys(Cbz)-OBzl; (f) Treating Boc-Lys(Bzl)-Val-Lys(Cbz)-OBzl of step (e) with trifluoroacetic acid to obtain H-Lys(Bzl)-Val-Lys(Cbz)-OBzl; (g) Coupling the H-Lys(Bzl)-Val-Lys(Cbz)-OBzl of step (f) with 3-O-acetyl Oleanoyl chloride (synthesized from 3-O-acetyl oleanolic acid and thionyl chloride) in the presence of triethylamine to get (3-O-Acetyl Oleanoyl)-Lys(Bzl)-Val-Lys(Cbz)-OBzl; (h) Hydrogenating the (3-O-Acetyl Oleanoyl)-Lys(Bzl)-Val-Lys(Cbz)-OBzl of step (g) in the presence of palladium and carbon catalyst in alcohol medium to get 3-O-Acetyl Oleanoyl-Lys-Val-Lys; (i) Hydrolyzing the acetyl group using a base to obtain a tripeptide of SEQ ID 1, linked to oleanolic acid, wherein SEQ ID #1 is K—V—K and structure 1 is as represented below:

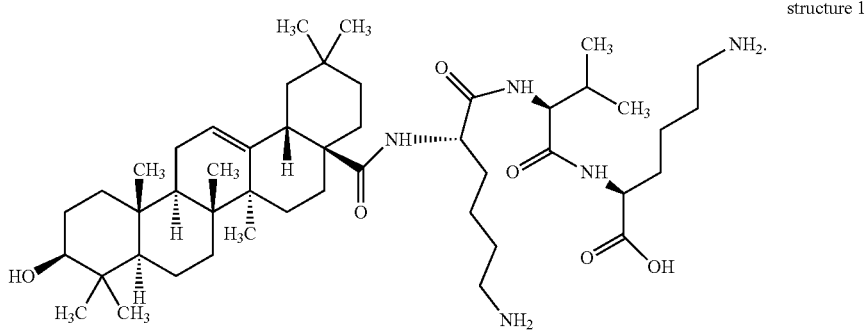

structure 1

In an aspect of the instant invention, there is provided a tripeptide of SEQ ID 1, linked to oleanolic acid as obtained from the above mentioned process.

In another aspect of the present invention, there is provided a method of preventing skin aging in mammals, said method comprising the steps of bringing into contact mammalian skin with effective concentration of tripeptide of SEQ ID 1 linked to oleanolic acid to prevent skin aging.

In one more aspect of the instant invention, there is provided a composition comprising a tripeptide of SEQ ID 1 attached to oleanolic acid formulated with pharmaceutically/cosmeceutically acceptable excipients, adjuvants, bases, diluents, carriers, conditioning agents, bioavailability enhancers, antioxidants and preservatives and/or incorporated into formulations containing anti-aging ingredients and administered topically in the form of creams, gels, lotions, powder, serum, oil, suspensions, ointments, soaps, scrubs, emulsions and compacts.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF THE DRAWINGS

The following drawings form a part of the present specification and are included to further illustrate aspects of the present disclosure. The disclosure may be better understood by reference to the drawings in combination with the detailed description of the specific embodiments presented herein.

DESCRIPTION OF THE MOST PREFERRED EMBODIMENTS

Figure 1:
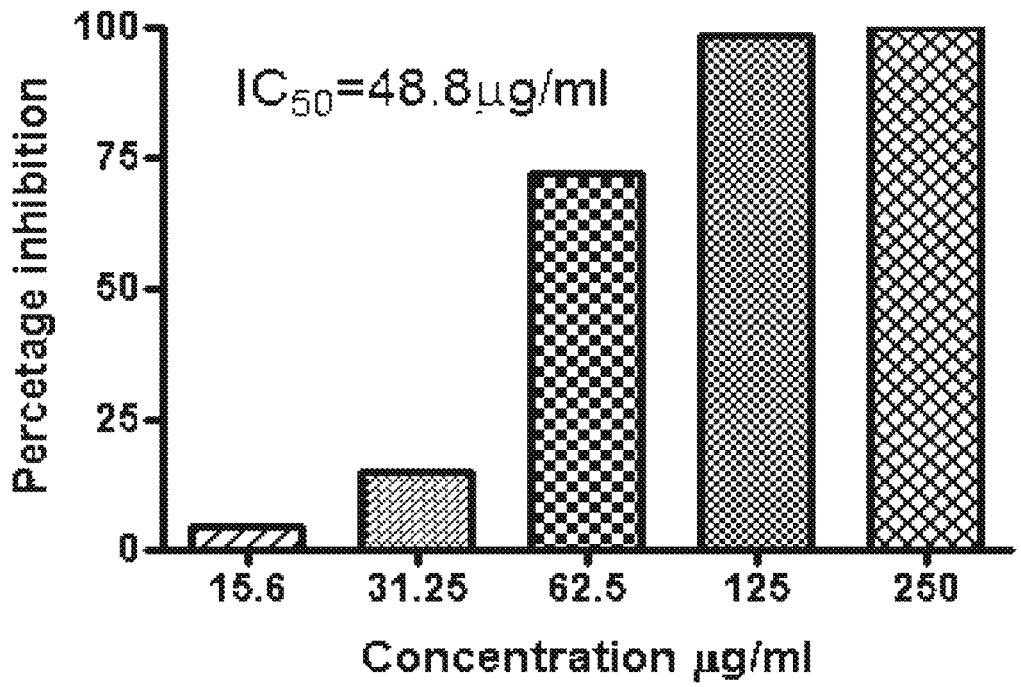
FIG. 1: depicts graphical representation of percent inhibition of collagenase activity shown by Lysin-Valine-Lysine (KVK) conjugated to oleanolic acid, in accordance with an embodiment of the present disclosure.

The present disclosure relates to oleanoyl tripeptide for skin care applications.

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

DEFINITIONS

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

Skin fibroblasts undergo substantial changes in their functional activity, morphology and proliferative potential during aging. Fibroblasts are responsible for the maintenance of Extra Cellular Matrix (ECM) and the physiological conditions of other skin layers. The number of dermal fibroblasts and their ability to synthesize soluble factors to maintain ECM decreases with aging. This results in skin thinning, loss of skin flexibility and elasticity, and wrinkle formation. Evaluating the proliferative potential of fibroblasts is of great significance to help physicians-cosmetologists to create an optimal skin care program.

TGF-β pathway is the major regulator of extracellular matrix production in human skin connective tissue. TGF-β increases collagen synthesis, keratinocyte proliferation, increases Elastin and Hyaluron, gives strength and resilience, reduces collagen degradation by decreasing matrix metalloproteases and improves skin thickness, firmness and elasticity.

In an embodiment of the present invention, there is provided a process for preparing tripeptide of structure 1 and SEQ ID 1 attached to oleanolic acid comprising the steps of: (a) Treating Boc-Lys(Cbz)-OH, wherein both the amino acid groups of L-Lysine is protected, with Benzyl bromide in Acetone and potassium carbonate to get Boc-Lys(Cbz)-OBzl; (b) Hydrolyzing the Boc-Lys(Cbz)-OBzl from step (a) to obtain H-Lys(Cbz)-OBzl.HCl; (c) Coupling the H-Lys (Cbz)-OBzl-HCl of step (b) with Boc-Val-OH in the presence of N, N'-Dicyclohexylcarbodiimide, Hydroxy benzotriazole and triethylamine to obtain Boc-Val-Lys(Cbz)-OBzl; (d) Treating Boc-Val-Lys(Cbz)-OBzl obtained from step (c) with trifluoroacetic acid to obtain H-Val-Lys(Cbz)-OBzl; (e) Coupling H-Val-Lys(Cbz)-OBzl of step (d) with Boc-Lys(Cbz)-OH in the presence of N, N'-Dicyclohexylcarbodiimide, Hydroxy benzotriazole and triethylamine to obtain Boc-Lys(Bzl)-Val-Lys(Cbz)-OBzl; (f) Treating Boc-Lys(Bzl)-Val-Lys(Cbz)-OBzl of step (e) with trifluoroacetic acid to obtain H-Lys(Bzl)-Val-Lys(Cbz)-OBzl; (g) Coupling the H-Lys(Bzl)-Val-Lys(Cbz)-OBzl of step (f) with 3-O-acetyl Oleanoyl chloride (synthesized from 3-O-acetyl oleanolic acid and thionyl chloride) in the presence of triethylamine to get (3-O-Acetyl Oleanoyl)-Lys(Bzl)-Val-Lys (Cbz)-OBzl; (h) Hydrogenating the (3-O-Acetyl Oleanoyl)-Lys(Bzl)-Val-Lys(Cbz)-OBzl of step (g) in the presence of palladium and carbon catalyst in alcohol medium to get 3-O-Acetyl Oleanoyl-Lys-Val-Lys; (i) Hydrolyzing the acetyl group using a base to obtain a tripeptide of SEQ ID 1, linked to oleanolic acid, wherein SEQ ID #1 is K—V—K and structure 1 is as represented below

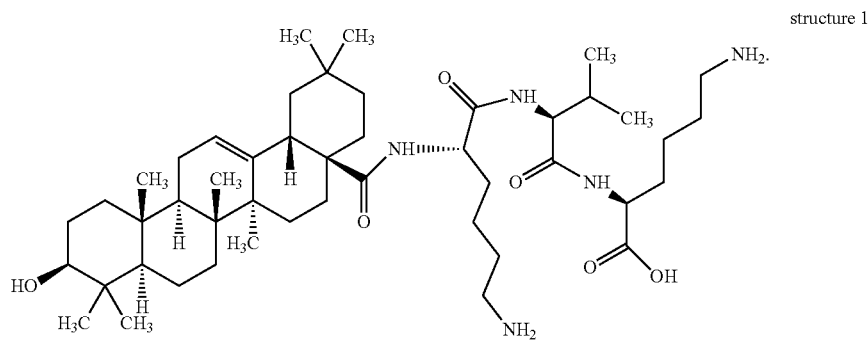

structure 1

In an embodiment of the present invention there is provided a method of preparing oleanoyl-KVK, wherein the base in step (i) is selected from the group consisting of sodium hydroxide, lithium hydroxide and potassium hydroxide.

In an embodiment of the present invention, there is provided a tripeptide of SEQ ID 1 linked to oleanolic acid as obtained from the process of claim 1.

In an embodiment of the present invention, there is provided a method of preventing skin aging in mammals, said method comprising steps of bringing into contact mammalian skin with effective concentration of tripeptide of SEQ ID 1 linked to oleanolic tripeptide, to prevent skin aging.

In an embodiment of the present invention, there is provided a method of preventing skin aging, wherein the symptoms of skin aging are selected from the group consisting of thinning of epidermis, decrease in melanocytes, loss of melanin production, loss of collagen and elastin, less oil production from sebaceous glands leading to loss of moisture and dryness, loss of subcutaneous fat layer, loss of insulation and padding, weak wound healing ability, sagging of skin, dryness, patchy skin, and lines.

In an embodiment of the present invention, there is provided a method of preventing skin aging wherein skin aging is prevented by inhibiting collagenase activity. Oleanoyl-KVK showed concentration dependent inhibition of collagenase enzyme.

In another embodiment of the present invention, there is provided a method of preventing skin aging, wherein skin aging is prevented by inhibiting collagenase activity.

In an embodiment of the present invention, there is provided a method of preventing skin aging, wherein skin aging is prevented by increasing skin fibroblast proliferation.

In an embodiment of the present invention, there is provided a method of preventing skin aging wherein skin aging is prevented by increasing collagen in skin fibroblasts.

In an embodiment of the present invention, there is provided a method of preventing skin aging, wherein skin aging is prevented by enhanced secretion of TGF-β by skin fibroblasts.

In an embodiment of the present invention, there is provided a composition comprising a tripeptide of SEQ ID 1 attached to oleanolic acid formulated with pharmaceutically/cosmeceutically acceptable excipients, adjuvants, bases, diluents, carriers, conditioning agents, bioavailability enhancers, antioxidants and preservatives and/or incorporated into formulations containing anti-aging ingredients and administered topically in the form of creams, gels, lotions, powder, serum, oil, suspensions, ointments, soaps, scrubs, emulsions, and compacts.

In an embodiment of the present invention there is provided a composition wherein said tripeptide is present in combination with other bioactive components.

In an embodiment of the present invention, there is provided a composition for preventing skin aging wherein said composition protects DNA from DNA damage and death. Apoptosis is a physiological process of programmed cell death involving fragmentation of DNA followed by cell death. UV light can accelerate premature aging and DNA damage. Exposure of skin cells to UVB light (290-320 nm) triggers cell death and fragmentation of DNA.

In an embodiment of the present invention, there is provided a method to prevent skin aging, wherein said method provides protection from oxidative stress. Oxidative stress is mainly caused by extrinsic factors like smoking, pollution, UV rays. All these factors induce ROS generation leading to oxidative stress and cellular damage.

In an embodiment of the present invention there is provided oleanoyl KVK as an anti aging peptide, wherein said tripeptide is present in combination with other bioactive components.

Although the subject matter has been described with reference to specific embodiments, this description is not meant to be construed in a limiting sense. Various modifications of the disclosed embodiments, as well as alternate embodiments of the subject matter, will become apparent to persons skilled in the art upon reference to the description of the subject matter. It is therefore contemplated that such modifications can be made without departing from the spirit or scope of the present subject matter as defined.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

Example 1: Anti Collagenase Activity

Material and Methods

Collagenase is one of the matrix metalloprotease, which digest collagen and other components of the extra cellular matrix (ECM). The ECM serves as a scaffold to stabilize the skin structure, and also helps in proliferation and metabolic functions of the skin cells. Loss of collagen leads to wrinkles and sagging of skin. The principle of the assay of collagenase inhibition is based on the fact that the substrate DQ™ gelatine is conjugated to fluorecein—a fluorescent compound. In DQ™ gelatine, fluorescence is quenched. DQ™ gelatine is efficiently digested by collagenases to yield a fluorescent compound which can be measured. The increase in fluorescence is proportional to enzyme activity. In the presence of an anti collagenase compound the amount of fluorescence will be decreased for a fixed concentration of enzyme and substrate.

Materials
    Equipment-BMG FLUOstar Optima (fluorescent Microplate reader)
    Reagents: Phosphate buffer (pH 7.4)
    Collagenase Enzyme assay kit (Enzchek® collagenase, gelatinase assay kit, Invitrogen, USA)
    Microtitre plates—96 well microtitre plates (black)—Corning, USA The assay was performed in a 96 well black microtitre plate. Type IV from *Clostridium histolyticum* with DQ gelatin as substrate was used for the assay. Different concentrations (15.6 to 250 µg/ml) of Oleanoyl-KVK were pre incubated with 20 µl of gelatin substrate (12.5 µg/ml). 100 µl of the Collagenase enzyme solution (final concentration- 0.4 U/ml) was added and the fluorescence intensity was measured at Em: 485 nm and Ex: 520 nm after 30 minutes. Enzyme activity of control (buffer) was recorded.

The percentage inhibition is calculated as follows:—

$$\% \text{ Inhibition} = \frac{(B - BC) - (T - C)}{(B - BC)} \times 100$$

B—Fluorescence in the presence of enzyme.
BC—Fluorescence in the absence of enzyme activity T—Fluorescence of enzyme activity in the presence of inhibitor
C—Fluorescence of the inhibitor alone Results:

The oleanoyl-KVK exhibited a dose dependent anti collagenase activity with an $IC_{50}$ at a concentration of 48.8 µg/ml (50% inhibition of enzyme activity) (FIG. 1). 100% inhibition of enzyme activity was seen at a concentration of 250 µg/ml. The results revealed that the Oleanoyl-KVK can preserve the extracellular matrix of the skin and prevent wrinkle formation and skin sagging, thereby preventing skin aging.

Example 2: Anti Elastase Activity

Material and Methods

Elastase is one of the matrix metalloproteinases, which digest elastin and other components of the extra cellular matrix and is important both for normal skin development. If this enzyme is not regulated by inhibitor proteins results in wrinkling of skin, premature ageing and carcinogenesis. The Anti-Elastase assay by Enz Chek elastase assay kit determines the elastase inhibitory activity of the products. The assays were done using the EnzChek elastase assay kit. The substrate is DQ elastin soluble bovine neck ligament. DQ elastin is labelled with BODIPY FL dye. The non-fluorescent substrate can be digested by elastase to yield highly fluorescent fragments and in the presence of inhibitor, the fluorescence intensity is quenched. The fluorescence intensity was measured in a microplate reader (emission at 485 nm and excitation at 520 nm.)

Materials

Equipment—BMG FLUOstar Optima (fluorescent Microplate reader)

Reagents: Phosphate buffer (pH 7.4)

Collagenase Enzyme assay kit (Enzchek® collagenase, gelatinase assay kit, Invitrogen, USA)

Microtitre plates—96 well microtitre plates (black)—Corning, USA

The assay was performed in a 96 well black microtitre plate. Elastase enzyme from pig pancreas and DQ Elastin as substrate was used for the assay. Different concentrations of oleanoyl-KVK were pre incubated with 50 µl of elastin substrate (25 µg/ml). 100 µl of the Elastase enzyme solution (final concentration-0.1 U/ml) was added and the fluorescence intensity was measured at Em: 485 nm and Ex: 520 nm after 30 minutes. Enzyme activity of control (buffer) was recorded.

The percentage inhibition is calculated as follows:—

$$\% \text{ Inhibition} = \frac{(B - BC) - (T - C)}{(B - BC)} \times 100$$

Figure 2:
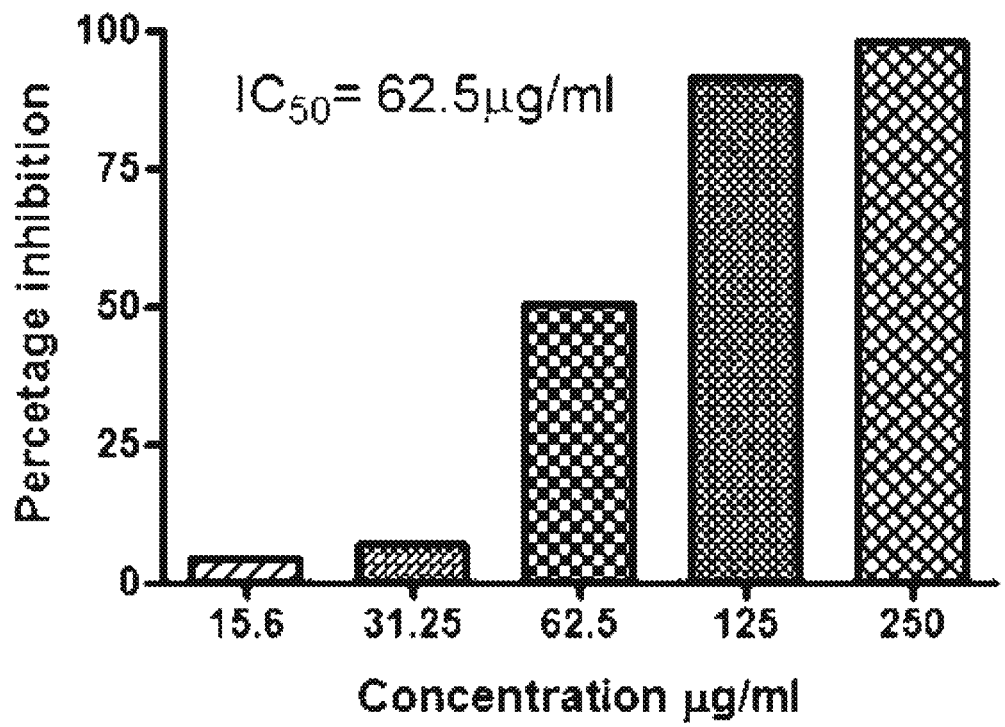
FIG. 2: depicts the graphical representation of percent inhibition of elastase activity shown by Lysin-Valine-Lysine (KVK) conjugated to oleanolic acid, in accordance with an embodiment of the present disclosure.

B—Fluorescence in the presence of enzyme
BC—Fluorescence in the absence of enzyme activity
T—Fluorescence of enzyme activity in the presence of inhibitor
C—Fluorescence of the inhibitor alone Result The oleanoyl-KVK exhibited a dose dependent anti collagenase activity with an $IC_{50}$ at 62.5 µg/ml (50% inhibition of enzyme activity) (FIG. 2). 98% inhibition of the enzyme activity was seen at a concentration of 250 µg/ml. The results showed that the Oleanoyl tripeptide can preserve the extracellular matrix of the skin and prevent wrinkle formation and skin sagging, by inhibiting enzyme elastase, thereby preventing skin aging.

Example 3: Increase in Proliferation of Fibroblast in the Presence of Oleanoyl KVK Skin fibroblasts undergo substantial changes in their functional activity, morphology and proliferative potential during aging. Fibroblasts are responsible for the maintenance of extracellular matrix (ECM) and the physiological conditions of other skin layers. The number of dermal fibroblasts and their ability to synthesize soluble factors to maintain ECM decreases with aging. This result in skin thinning, the loss of skin flexibility and elasticity, and wrinkle formation. Evaluating the proliferative potential of fibroblasts is of great significance to help physicians-cosmetologists to create an optimal skin care.

Material and Methods

Human dermal fribroblasts were seeded at a density of $5 \times 10^3$ cells/well in DMEM 10% FBS and antibiotics in 96 well plate and allowed to form a monolayer in a humidified incubator at 37° C. and 5% $CO_2$ atmosphere for 24 hours. Cells were treated with different concentration of the extract for 72 hours to assess the cytotoxicity. The viability of fibroblasts were determined by SRB assay (Nature protocols, 2006, 1, 3, 2112-16). Cells in DMEM with 0.1% DMSO was used as positive control while media without cells were used as negative control $$\text{Percentage increase } (\%) = \frac{\text{Absorbance (sample)} - \text{Absorbance (negative control)}}{\text{Absorbance (negative control)}} \times 100$$

Results

Figure 3:
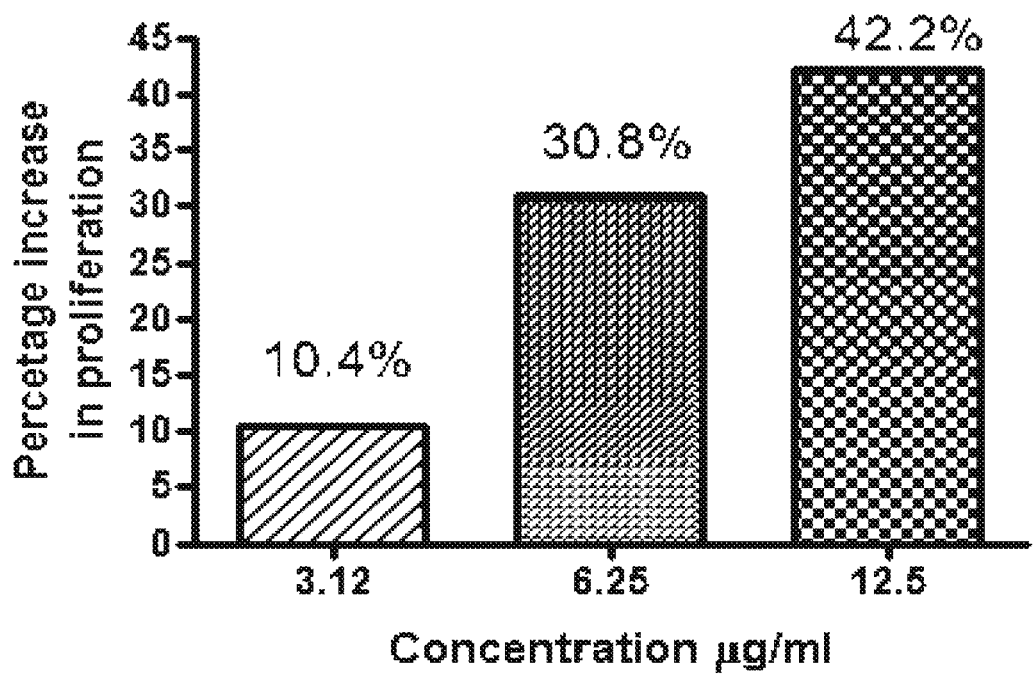
FIG. 3: depicts the graphical representation of percent increase in proliferation of fibroblast shown by Lysin-Valine-Lysine (KVK) conjugated to oleanolic acid, in accordance with an embodiment of the present disclosure.
Figure 4A:
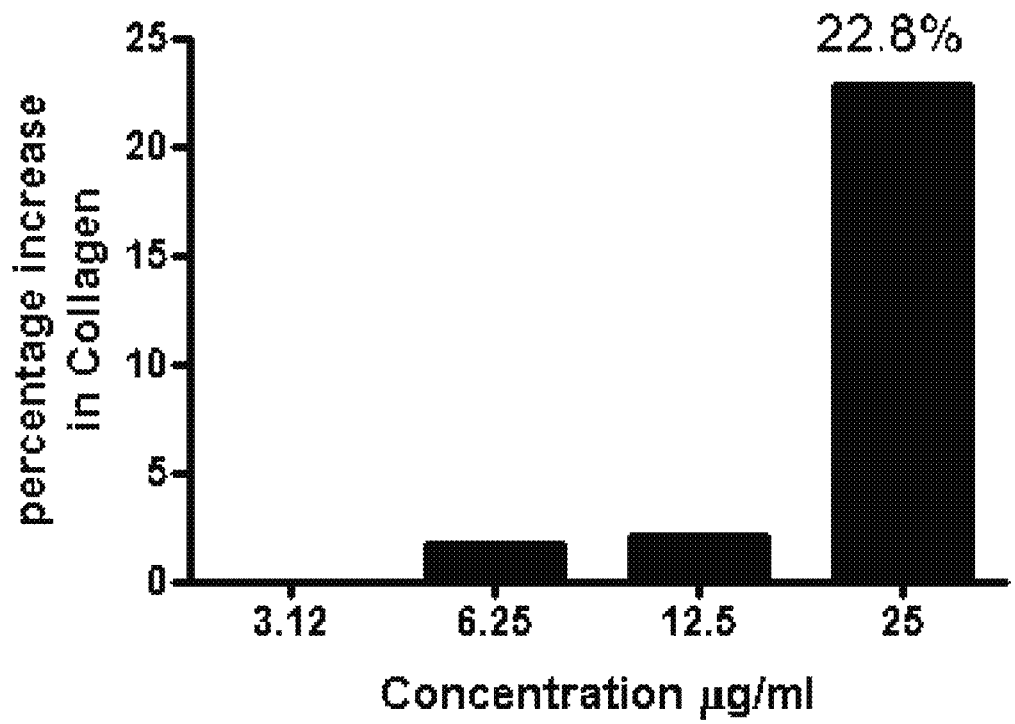
FIG. 4a depicts the graphical representation of the percent increase in collagen production in fibroblasts shown by Lysin-Valine-Lysine (KVK) conjugated to oleanolic acid, FIGS. 4b (Control) and 4c (treated with oleanoyl KVK) are pictorial representation percent increase in collagen staining in fibroblasts, in accordance with an embodiment of the present disclosure.
Figure 4B:
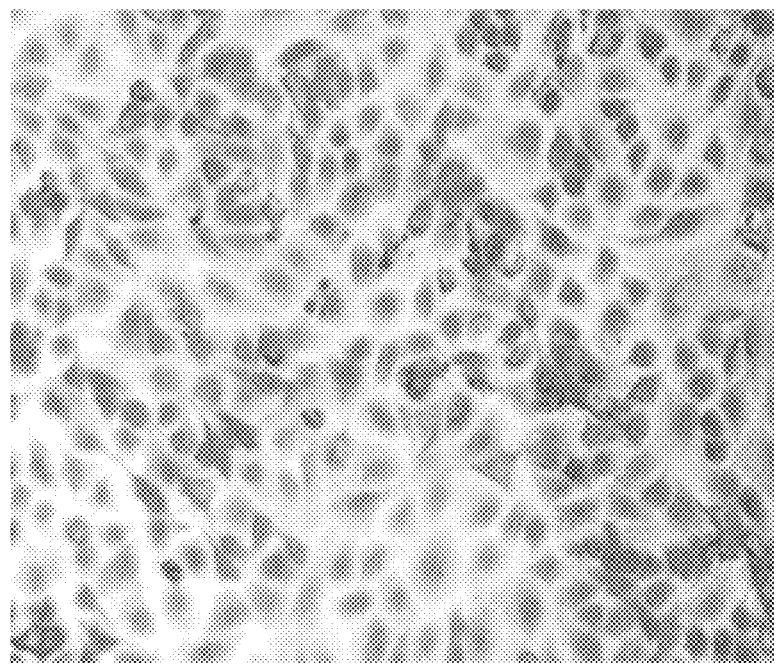
FIG. 4.
Figure 4C:
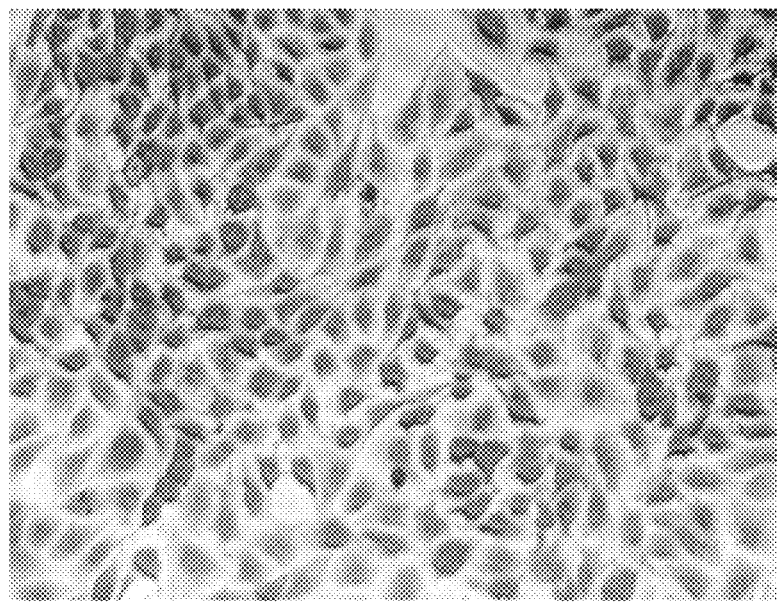
Figure 5:
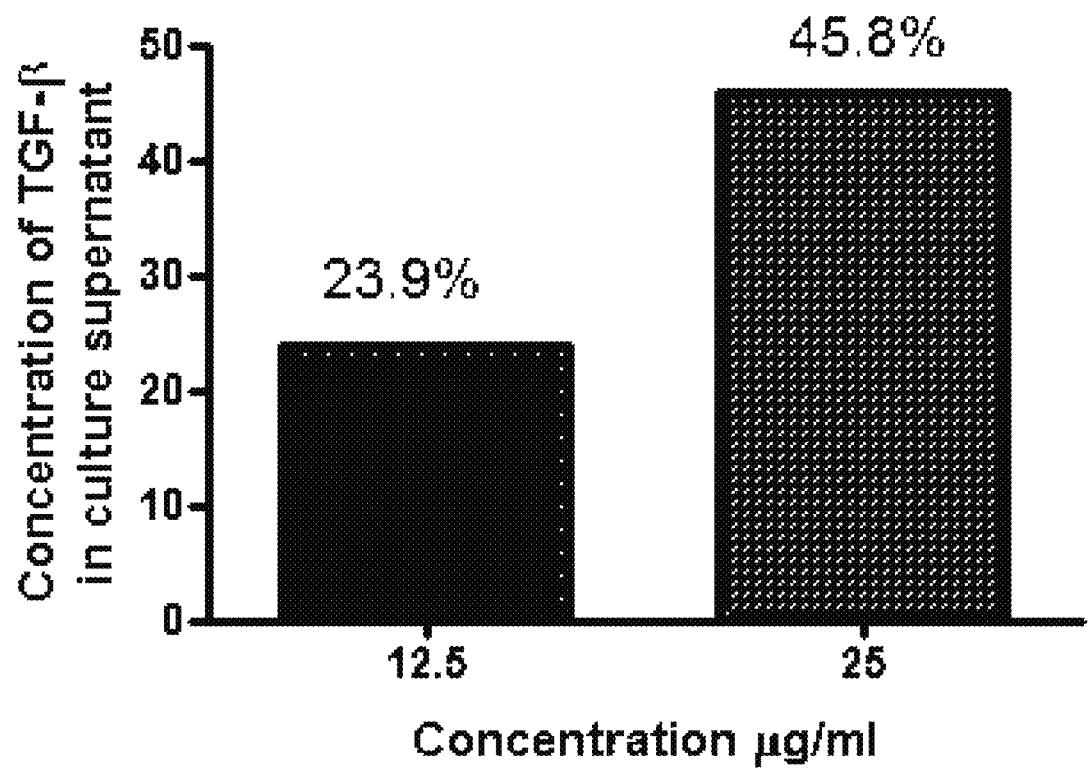
FIG. 5: depicts the graphical representation of the concentration of TGF-β concentration in culture supernatant shown by Lysin-Valine-Lysine (KVK) conjugated to oleanolic acid, in accordance with an embodiment of the present disclosure.

Oleanoyl-KVK showed dose dependent increase in proliferation of fibroblasts (FIG. 3). At a concentration of 12.5% there was 42.2% increase in proliferation of fibroblasts. FIGS. 4a and 4b provides the percent increase in collagen production in fibroblasts. Oleanoyl-KVK showed 22.8% increase in collagen staining in fibroblasts. FIG. 5 shows the concentration of TGF-β fibroblasts in the fibroblast culture supernatant. Oleanoyl-KVK showed a dose dependent increase in TGF-β secretion by fibroblasts.

Example 4: Protection Against UV Radiation

Material and Methods

UVB is responsible for the tanning effects of human skin and had been considered mostly harmless for many years. UV radiation has broad spectrum, ranging from 40 to 400 nm (30-3 eV), which is divided into Vacuum UV (40-190 nm), Far UV (190-220 nm), UVC (220-290 nm), UVB (290-320), and UVA (320-400 nm), of which the latter two are medically important. There are two distinct subtypes of UVA radiation. Short-wave UVA (320-340 nm) and long-wave UVA (340-400 nm) constitute most of UVA radiation. The amount of exposure to UVA usually remains constant, whereas UVB exposure occurs more in the summer UV radiations are responsible for high incidence of premature skin aging, referred to as photo-aging, as well as skin cancer and melanoma. UVB irradiation has been demonstrated to produce ROS in the cells and skin, which induces the synthesis of matrix metalloproteinases (MMPs), causing photo-aging effects in skin. The effects of UVA manifest usually after a long duration of exposure, even if doses are low. It has been postulated that UVA up regulates the formation of matrix metalloproteinase (MMPs), enzymes that degrade the matrix protein's elastin and collagen, which, if not prevented, can result in marked reduction in skin elasticity and increased wrinkling UVA can penetrate deeper into the skin in comparison to UVB and contributes to photo-aging, photo-carcinogenesis and photo-dermatosis and increase in reactive oxygen species (ROS) in fibroblasts and cells which are deeper inside the skin.

Materials

Cells: Human keratinocytes (HaCAT)—cells were maintained as a monolayer culture in Dulbeccos modified minimal essential medium (DMEM) Life technologies, CA, USA) supplemented with 10% (v/v) heat-inactivated foetal bovine serum (FBS; GIBCO/Invitrogen, Carlsbad, Calif.), 100 units/mL penicillin and 100 µg/mL streptomycin (Life technologies) at 37° C. in a humidified 5% $CO_2$ incubator.

Reagents: Dulbeccos modified minimal essential medium (DMEM), Fetal bovine serum (FBS), Annexin-FITC, Propidium Iodide-Apoptosis detection kit, Biovision, USA.

Instrument: Flow Cytometry (BD-FACS-Celesta).

Procedure

Cells ($3 \times 10^5$) were pre-treated with different concentrations of test sample for one hour and exposed to UVB. Cells were exposed to UVB rays for 10 min and incubated for 16 hours in DMEM with 2% serum. Cells were labelled with annexin-FITC and propidium iodide (PE) for 10 minutes in dark and analyzed using flow cytometer (BD FACS-Celesta).

Results

Figure 6A:
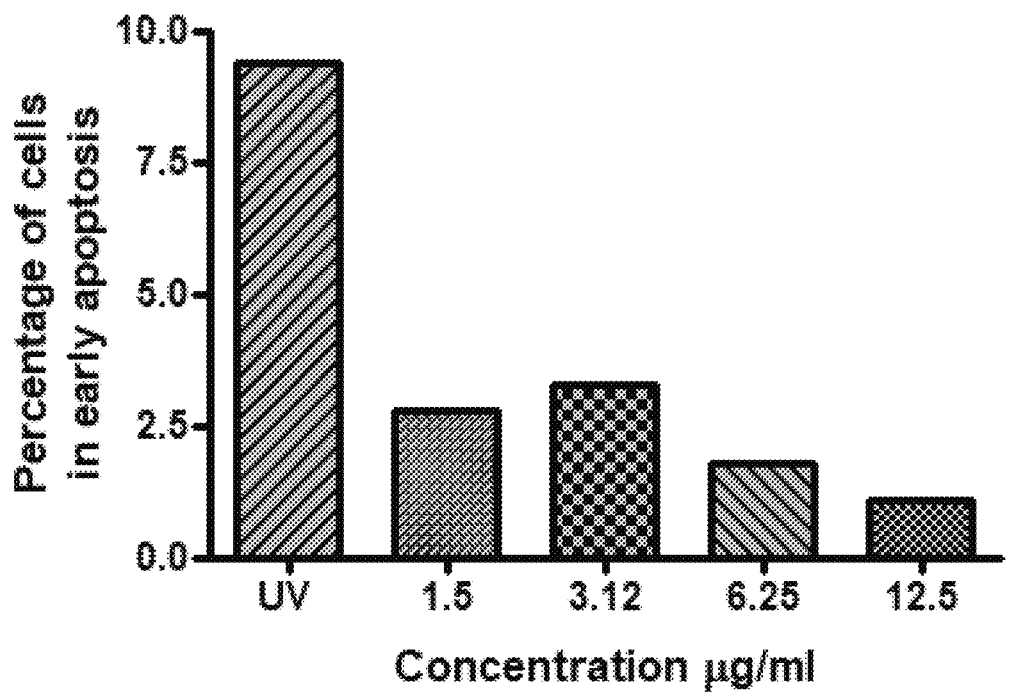
FIG. 6: depicts the graphical representation of protection from UV induced DNA damage shown by Lysin-Valine-Lysine (KVK) conjugated to oleanolic acid. (6a) Reduction in early Apoptosis; (6b) Reduction in late apoptosis; (6c) Increase in Live cells; (6d) protection against UV induced DNA damage and death, in accordance with an embodiment of the present disclosure.
Figure 6B:
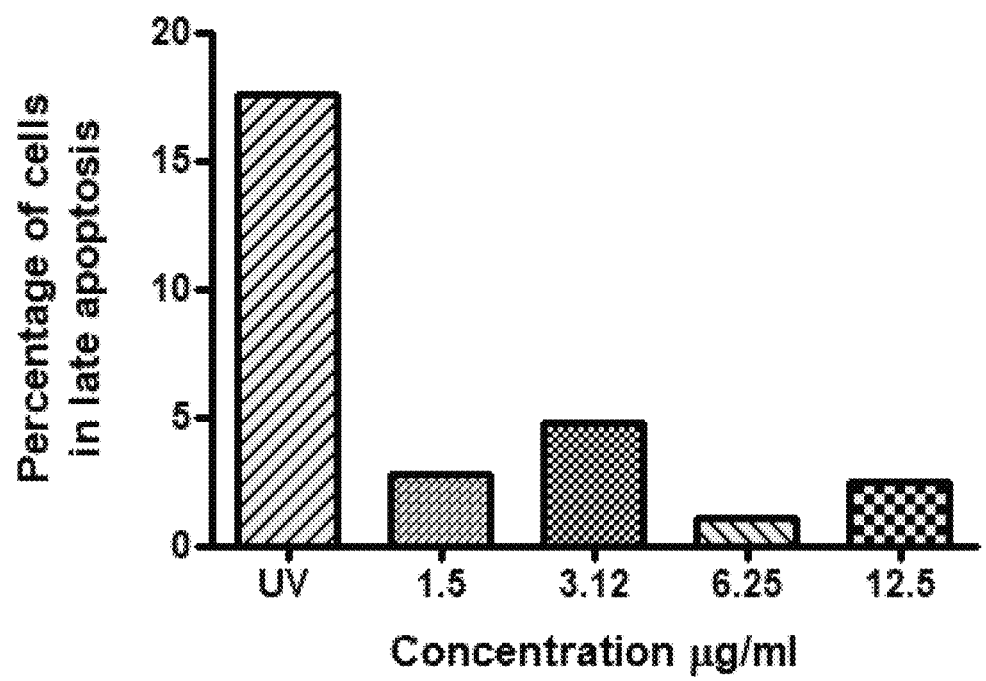
Figure 6C:
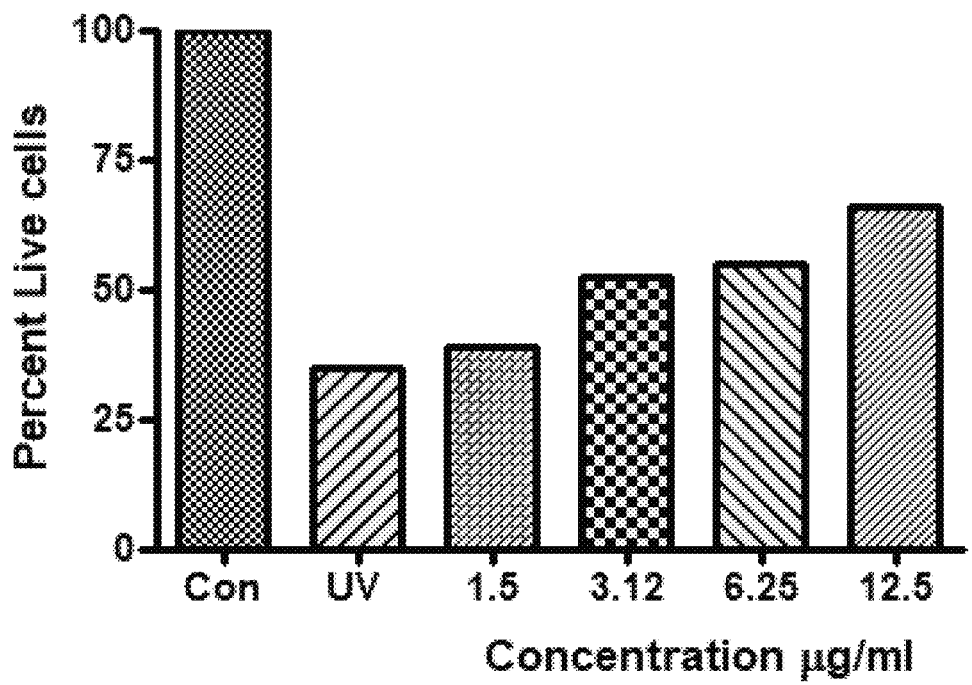
Figure 6D:
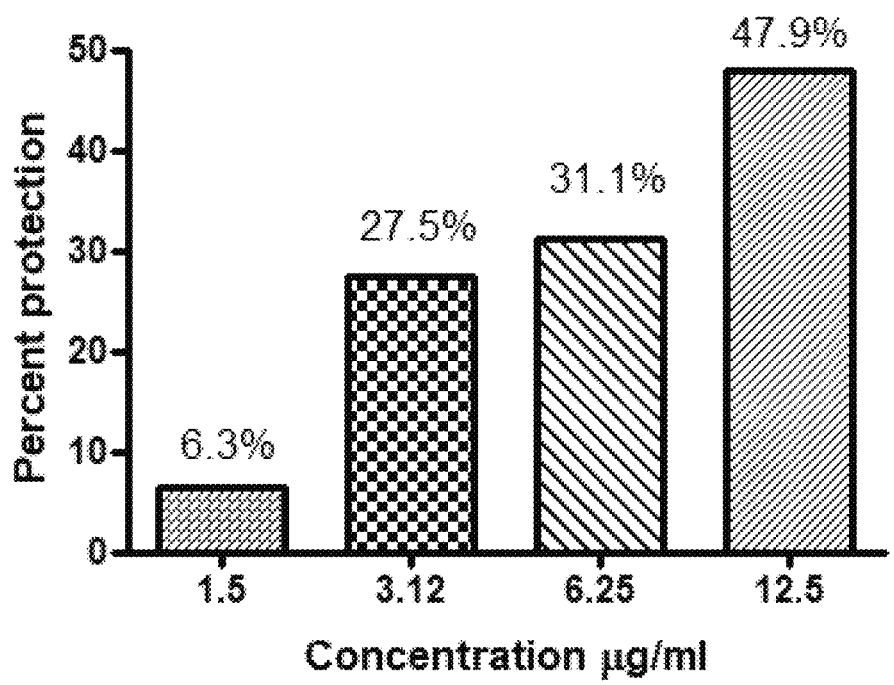

The results showed that the oleanoyl-tripeptide protects keratinocyte cells from UVB induced toxicity (FIGS. 6a, 6b, 6c and 6d) and (FIGS. 7a, 7b, 7c, and 7d) and has potent use and benefits as an UV protective agent in cosmetic applications. As evident from FIG. 6a there is a concentration dependent reduction in early apoptosis and at a concentration of 12.5 µg/ml showed the maximum reduction in early apoptosis. FIG. 6b shows the concentration dependent reduction in late apoptosis, similar results were obtained in this case also. FIG. 6c shows the percent increase in live cells upon treatment with different concentrations of oleanoyl tripeptide. A concentration of 12.5 µg/ml showed the highest increase in live cells. FIG. 6d shows the percent protection against UV induced DNA damage and death. A concentration of 12.5 µg/ml provided a percent protection of 47.9%.

Figure 7:
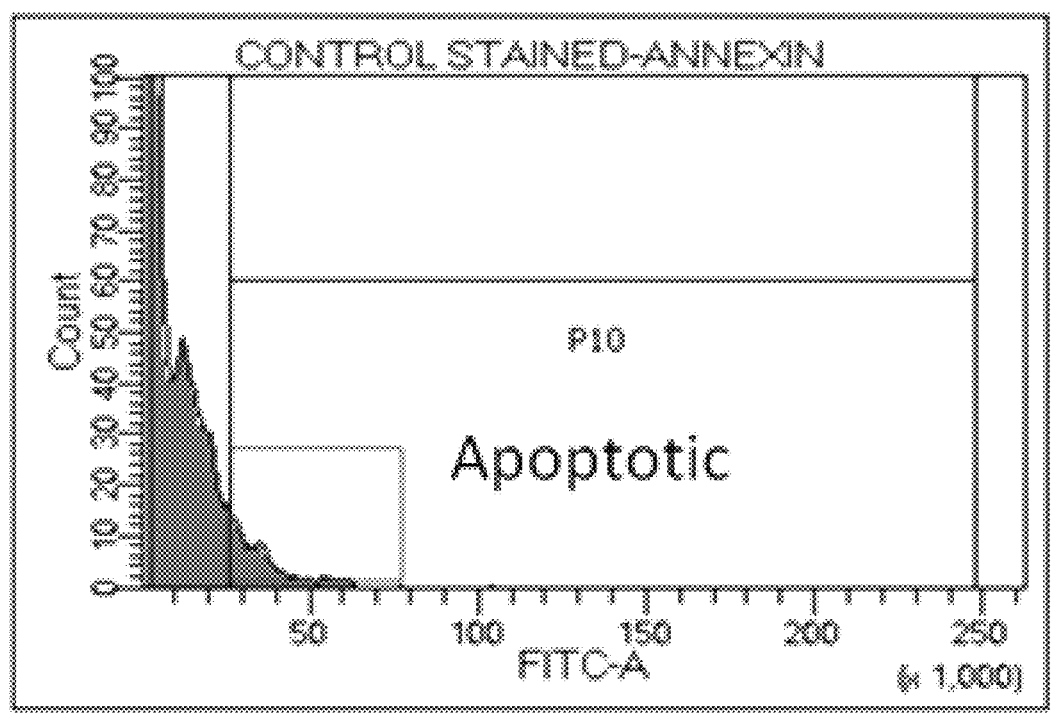
FIG. 7: depicts the flow cytometric graphs showing protection from UV induced DNA damage and death of treated and untreated samples, in accordance with an embodiment of the present disclosure.
Figure 7:
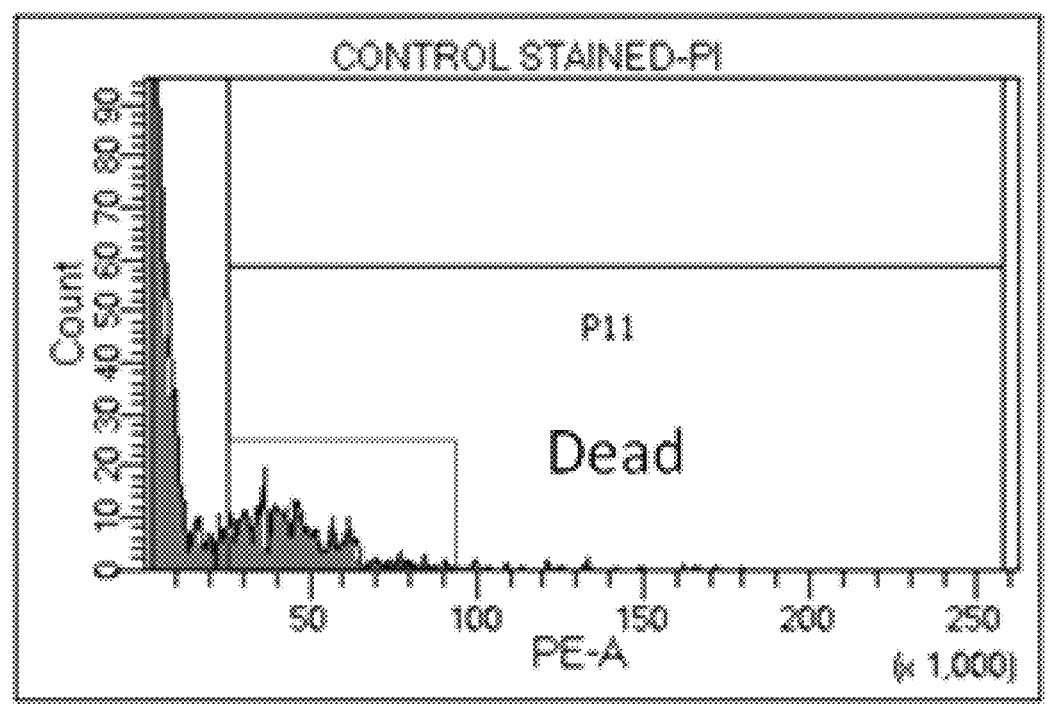
Figure 7:
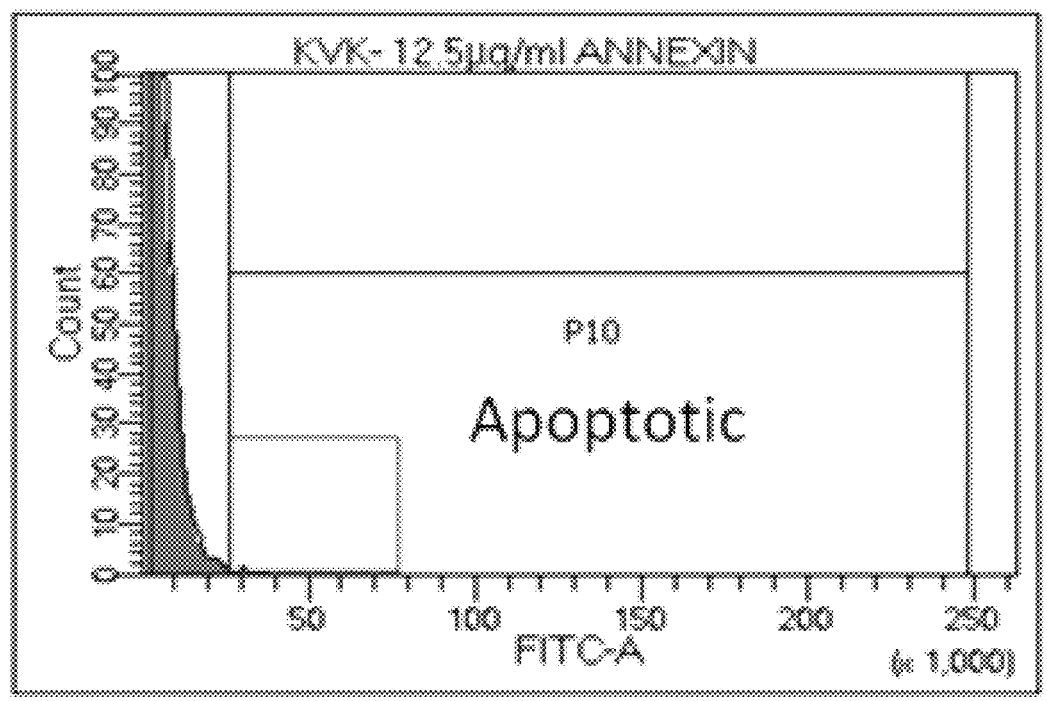
Figure 7:
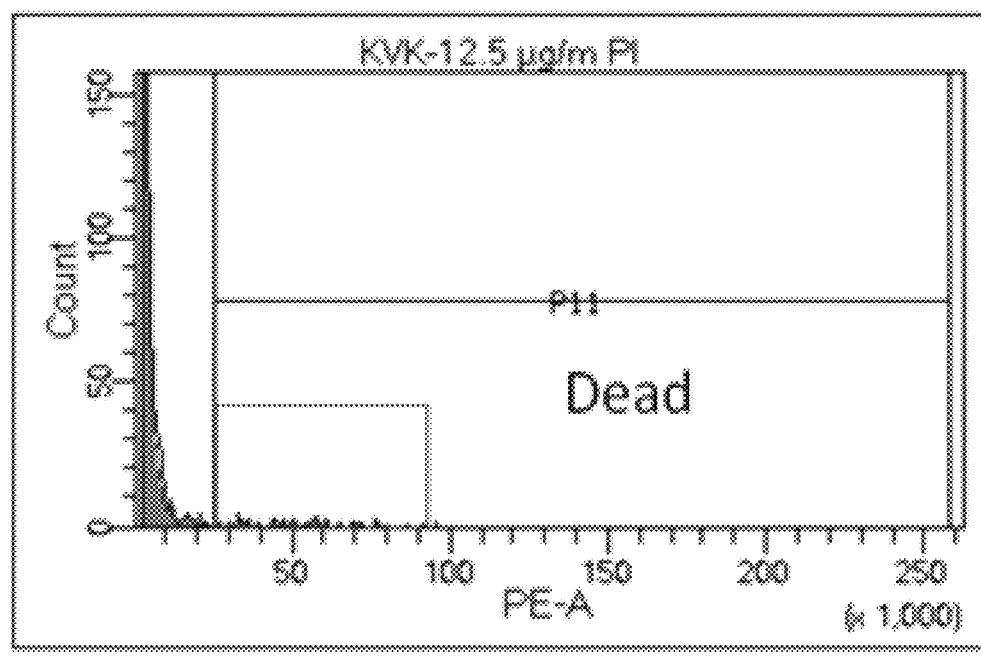

FIG. 7 represents the flow cytometry graphs showing the apoptotic and dead cells with and without treatment. Oleanoyl KVK protected keratinocytes from apoptosis and DNA damage induced by UVB radiation. At a concentration of 12.5 µg/ml protection from UV induced cell damage was found to be 47.9%.

Example 5: Protection from Oxidative Stress

Material and Methods

Skin cells are constantly exposed to reactive oxygen species (ROS) and oxidative stress from exogenous and endogenous sources. UV radiation is the most important environmental factor in the development of skin cancer and skin aging. Oxidative stress is developed in skin when the UV-induced generation of ROS exceeds the ability of endogenous defence mechanism. The reduction of oxidative stress can be achieved either by lowering exposure to UVR and/or by increasing levels of antioxidant defence mechanism. Melanin present in the skin and the anti oxidant enzymatic reactions protect our skin from oxidative stress. Many studies have shown treatment with antioxidants prior to UV exposure can prevent oxidative damage to cellular biomolecules.

Cells: Human keratinocytes (HaCAT)—cells were maintained in fibroblast media (Gibco) at 37° C. in a humidified 5% $CO_2$ incubator.

Reagents: Keratinocyte media (Gibco) DCFH-DA Instrument: FluoStar Optima microplate reader.

Procedure

Reactive oxygen species include a number of molecules that damage DNA and RNA and oxidize proteins and lipids (lipid peroxydation). These reactive molecules contain an oxygen atom/molecule and include $H_2O_2$ (hydrogen peroxide), NO (nitric oxide), $O_2^-$ (oxide anion), peroxynitrite ($ONOO^-$), hydrochlorous acid (HOCl), and hydroxyl radical (OH). 5-(and 6)-chloromethyl-20, 70-dichlorohydrofluorescein diacetate (CM-H2DCFDA) freely permeates the plasma membrane and is hydrolyzed in the cytosol to form the DCFH carboxylate anion. Oxidation results in the formation of fluorescent DCF, which is maximally excited at 495 nm and emits at 520 nm.

Keratinocytes were seeded at 50,000 cells per well in 96 well black plates and allowed to grow as a monolayer for 24 hours. Cells were pre-treated with different concentration of Oleanoyl-KVK for one hour. The plate was exposed to UVA radiation for 1 hour. Freshly prepared DCFH-DA reagent was added to all the wells (2 ug/well). The plate was incubated at 37° C. for 30 minutes. Fluorescence was recorded at 485:520, Ex: Em wavelength in FluoStar Optima microplate reader.

Results

Figure 8A:
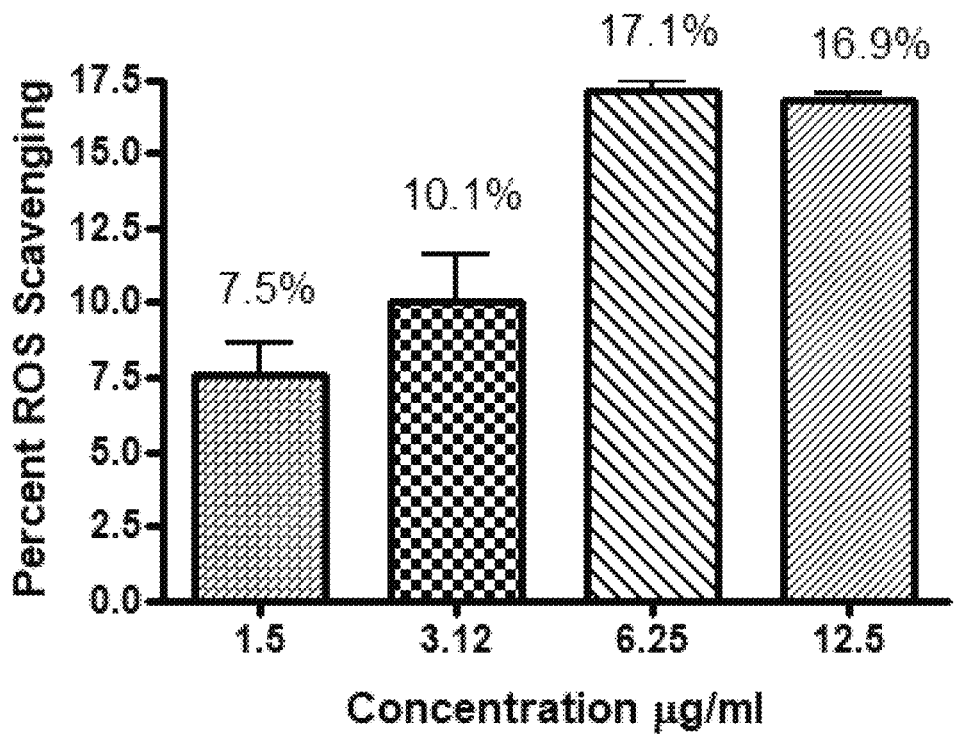
FIG. 8: depicts the graphical representation of the protection from oxidative stress as shown by Oleanoyl KVK. (Sa) Percent ROS scavenging induced by UVB; (8b) percent ROS scavenging induced by heavy metals, in accordance with an embodiment of the present disclosure.
Figure 8B:
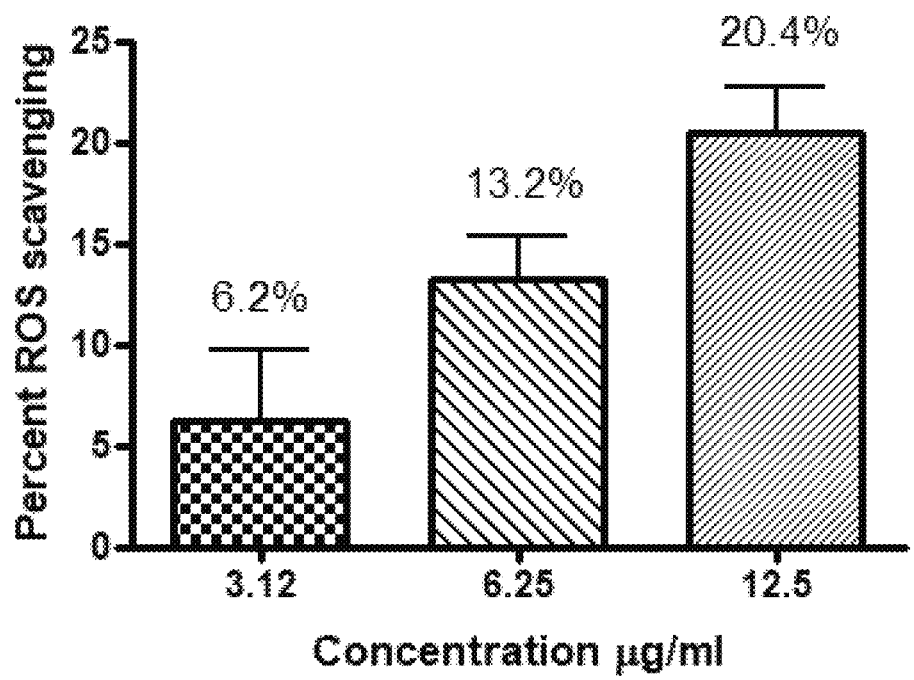

Oleanoyl KVK afforded protection against oxidative stress induced by extraneous agents including UV radiation and pollutants like heavy metals. As evident from FIG. 8a at a concentration of 6.25 µg/ml of oleanoyl-KVK showed 17.1% ROS scavenging activity to the UV induced stress. Similarly a concentration of 12.5% of the oleanoyl tripeptide provides 20.4% ROS scavenging to that induced by heavy metals (FIG. 8b). Thus this can be used as an anti pollutant in cosmetic formulations.

Example 6: Gene Expression Analysis

Dermal fibroblasts are crucial cellular components for the structural integrity of the skin. The extracellular matrix contains collagen, elastin and hyaluron which determine the integrity of skin. Hyaluronan (HA) synthesized by hyaluronan synthases which add UDP-glucosamine and UDP-glucuronic acid residues to a growing HA polymer chain. Transforming growth factor (TGF-β) plays a central role in ECM biosynthesis and controls collagen homeostatis by regulation of both collagen synthesis and degradation. Epidermal growth factor stimulates cell growth and induces collagen synthesis. The expression pattern of these genes in dermal fibroblasts and keratinocytes in the presence of oleanoyl KVK compared to untreated control was studied.

Material and Methods

Materials:

Human dermal keratinocyte cells, 6 well microtiter plates, fibroblast growth media, trizol, can synthesis kit, SYBR green master mix for RT-PCR.

Methods

Human dermal fibroblasts and keratinocytes were cultured in 6 well microtiter plates in the presence of 6.25 µg/ml oleanoyl KVK for 24 hours. Untreated cells were used as control. At the end of incubation time, the cells were lysed and RNA was extracted.

RNA Extraction:

Cells were harvested after second progression on day 7 and total RNA was extracted using the Trizol method. Extracted RNA was treated with DNAse I to remove any contaminating DNA and again extracted using phenol: chloroform: isoamyl alcohol extraction (24:25:1). Quality of RNA was determined by checking the absorbance at 260/280 nm using a Nanodrop (Thermo).

Quantitative Real Time PCR:

2 μg of total RNA was taken for cDNA synthesis using Super Script III First-Strand Synthesis System (Life Technologies). Quantitative RT-PCR analysis was performed to determine the expression of brown fat specific genes in Roche Light cycler 96 using SYBR Green master mix (Thermo Scientific). β actin was used as a house keeping gene. The relative RNA abundance of the genes was normalized to the housekeeping β actin gene and expressed as delta delta CT (equivalent to fold change transformed by $Log_2$).

Figure 9:
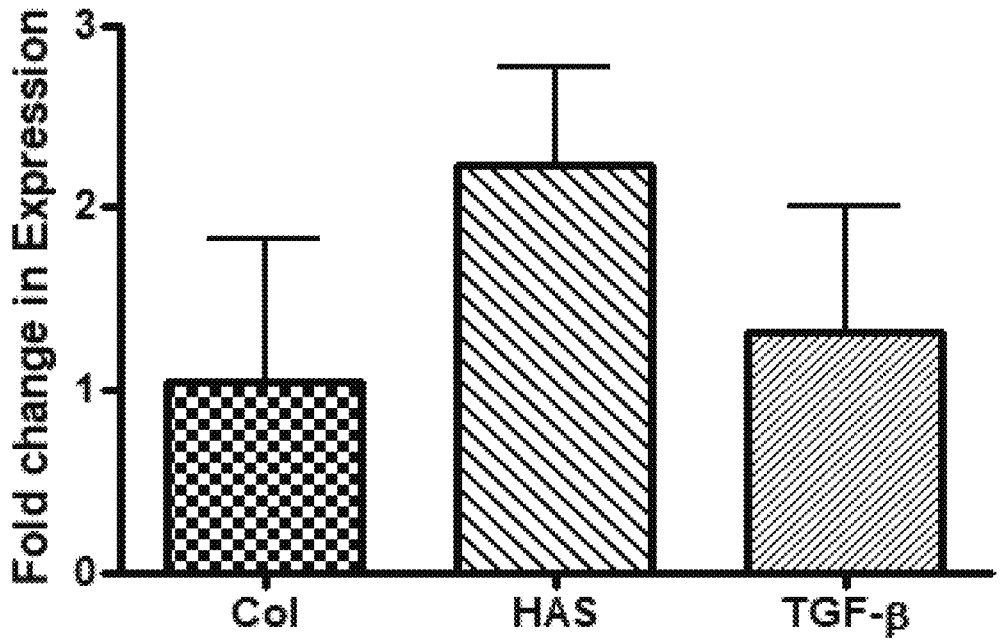
FIG. 9: depicts the graphical representation of the increased expression levels of collagen, TGF-β and hyaluronan synthase in human dermal fibroblasts, in accordance with an embodiment of the present disclosure.
Figure 10:
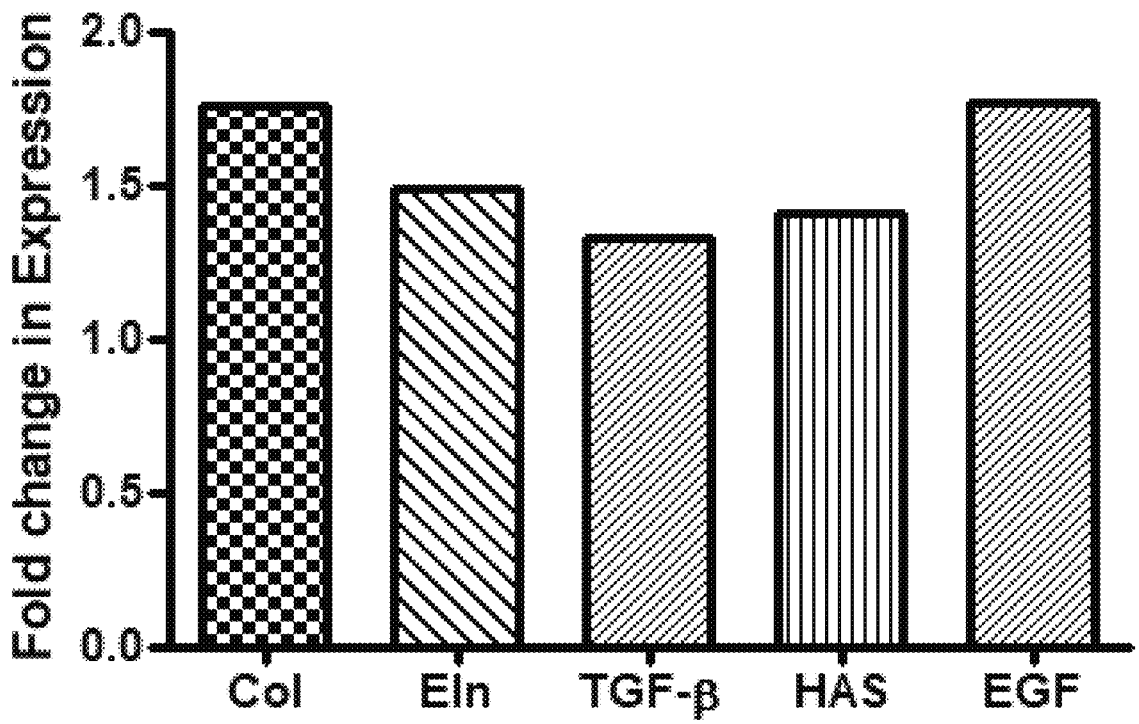
FIG. 10: depicts the graphical representation of increased expression of collagen, Elastin, TGF-β, hyaluronan synthase and epidermal growth factor by keratinocytes, in accordance with an embodiment of the present disclosure.
Figure 11:
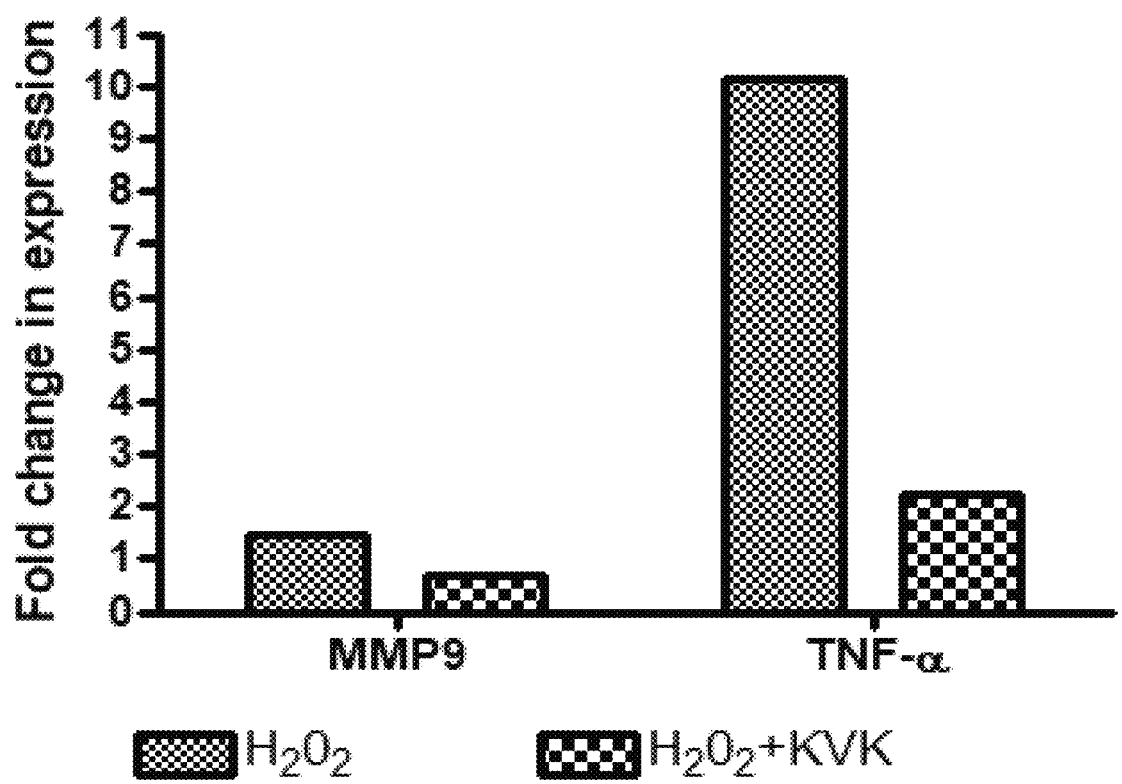
FIG. 11: depicts the graphical representation of oxidative stress induced increase in expression of matrix metalloprotease and tumour necrosis factor by keratinocytes, and their inhibition by treatment with oleanoyl KVK in accordance with an embodiment of the present disclosure, in accordance with an embodiment of the present disclosure.

FIG. 9 shows the Fold change in gene expression in dermal fibroblasts. Oleanoyl KVK increased the expression level of collagen, TGF-β and hyaluronan synthase in human dermal fibroblasts. FIG. 10 shows the fold change in gene expression in keratinocytes. Oleanoyl KVK increased the expression of keratinocytes. FIG. 11 shows the gene expression in keratinocytes exposed to oxidative stress. Oxidative stress induces the expression of inflammatory markers and extra cellular matrix degrading metalloproteases. Treatment with oleanoyl KVK down regulated the expression levels of matrix metalloprotease 9 and tumor necrosis factor α in human dermal fibroblasts.

Skin inflammation can result from exposure to UV or ionizing radiation, allergens, or to contact with chemical irritants or allergens. When the skin is exposed to an inflammatory agent, the cells in the skin produce an inflammatory messenger known as cytokine. These cytokines trigger an inflammatory cascade which produce other cytokines activate the blood cells, produce free radicals which damage the skin.

Principle of the Assay

Anti inflammatory activity was examined using human monocyte/macrophage cell line THP-1. Monocytes respond to lipo-polysaccharides (LPS) by secreting pro-inflammatory cytokines. Tumour necrosis factor (TNF-α) is one of the principle cytokine which triggers a cascade of inflammatory reactions. The concentration of TNF-α was measured using an Enzyme linked Immunosorbent assay (ELISA). Reduction in TNF-α concentration indicates an anti inflammatory activity of the compound.

Materials

Cells: THP1-human monocytes purchased from American Type Culture Collection (ATCC, Manassas, Va.) and maintained as a monolayer culture in Rosewell park memorial institute Medium (RPMI Life technologies, CA, USA) supplemented with 10% (v/v) heat-inactivated foetal bovine serum (FBS; GIBCO/Invitrogen, Carlsbad, Calif.), 100 units/mL penicillin and 100 μg/mL streptomycin (Life technologies) at 37° C. in a humidified 5% $CO_2$ incubator.

Reagents and buffers: Lipopolysaccharide (LPS, Sigma chemicals, USA), Phosphate buffered saline, RPMI, FBS, ELISA kit: Human TNF ELISA kit, Krishgen Biosciences, USA Methods $1 \times 10^5$ THP-1 cells were stimulated with 100 ng with lipopolysacharide (LPS, 0.1 μg/mL) to induce TNF-α secretion. Cells were pre treated with different concentrations of oleanoyl KVK before LPS treatment. The cell supernatants were collected 24 hour after treatment and secreted TNF-α as estimated by cytokine ELISA as described by the manufacturer. Un-stimulated cells were used as negative control. The limit of detection was <1 pg/mL.

Results

| Oleanoyl KVK Concentration(μg/ml) | % Inhibition | Cell viability |
| --- | --- | --- |
| 12.5 | 71.03 | 100% |
| 6.25 | 31.01 | 100% |
| 3.12 | 12.53 | 100% |
| 1.56 | 12.14 | 100% |

CONCLUSION

Oleanoyl KVK showed anti inflammatory activity with an IC50 of 9.09 μg/ml.

Example 7: Formulations Containing Oleanoyl-KVK for Skin Care

The composition containing the oleanoyl-KVK may be formulated with pharmaceutically/cosmeceutically acceptable excipients, adjuvants, bases, diluents, carriers, conditioning agents, bioavailability enhancers, antioxidants and preservatives and/or incorporated into formulations containing anti-aging ingredients and administered topically in the form of creams, gels, lotions, powder, serum, oil, suspensions, ointments, soaps, scrubs, emulsions, and compacts.

In a related aspect, one or more skin care ingredients are selected from the group consisting of, but not limited to, Alpha Lipoic Acid, oxyresveratrol, Beet root extract, *Boswellia serrata* Extract, β boswellic acids, *Boswellia serrata* oil, *Centella asiatica* Extract, triterpenes, *Garcinia indica* extract, anthocyanins, *Cocos nucifera* extract and juice, *Coleus forskohlii* Extract, forskolin, *Coleus forskohlii* Oil, Tetrahydropiperine, Ellagic Acid, Gallnut Extract, polyphenols, Galanga Extract, Glycyrrhizinic Acid, Green Tea Extract, Epigallocatechin Gallate, Licorice extract, Mono-Ammonium Glycyrrhizinate, Limonoids, Oleanolic Acid, Oleuropein, *Piper longumine* extract, piperine, Ellagic acid, Pomegranate Extract (Water Soluble), pterostilbene, resveratrol, *Pterocarpus santalinus* extract, Rosemary Extract, Rosmarinic Acid, Amla extract, beta glucogallin, tetrahydrocurcumin, *Salvia Officinalis* (Sage) Leaf Extract, Ursolic Acids, Saponins, *Sesamum indicum* (Sesame) Seed Extract, Sesamin and sesamolin, moringa oil, moringa seed extract, Horse Chestnut Extract, Vitex Oil, Xymenynic Acid, ethyl ascorbic acid, Argan oil, Lemon peel extract, turmeric oil, Barley Beta Glucans, coenzyme Q10, olive oil, avocado oil and cranberry oil.

In another related aspect, one or more anti-oxidants and anti-inflammatory agents are selected from the group consisting of, but not limited to, vitamin A, D, E, K, C, B complex, rosmarinic acid, Alpha Lipoic Acid, oxyresveratrol, Ellagic Acid, Glycyrrhizinic Acid, Epigallocatechin Gallate, plant polyphenols, Glabridin, moringa oil, oleanolic acid, Oleuropein, Carnosic acid, urocanic acid, phytoene, lipoid acid, lipoamide, ferritin, desferal, billirubin, billiverdin, melanins, ubiquinone, ubiquinol, ascorbyl palmitate, Mg ascorbyl phosphate, ascorbyl acetate, tocopherols and derivatives such as vitamin E acetate, uric acid, α-glucosyl-rutin, calalase and the superoxide dismutase, glutathione, selenium compounds, butylated hydroxyanisole (BHA), butylated hydroxytoluene (BHT), sodium metabisulfite (SMB), propyl gallate (PG) and amino acid cysteine.

In another related aspect, one or more bioavailability enhancers are selected from the group, but not limited to, piperine, tetrahydropiperine, quercetin, Garlic extract, ginger extract, and naringin.

Tables 1-10 provide illustrative examples of skin care formulations containing oleanoyl-KVK.

TABLE 1

Skin Care Lotion

Active Ingredients

Oleanoyl-KVK
Tetrahydrocurcumin, licorice extract, Pterostilbene, Tetrahydropiperine, *Galanga* extract, Niacinamide
Other ingredients/Excipients Aqua, Avobenzone, Octyl methoxy cinnamate, Octocrylene, Benzophenone-3, Octyl Salicylate, Glyceryl Stearate SE, Sorbitan Stearate & Sucrose Cocoate, Polysorbate 20, Glycerin, Cetostearyl Alcohol, Cetearyl Olivate (and) Sorbitan Olivate, Stearic acid, Isopropyl myristate, *Garcinia indica* Seed Butter, Caprylic/Capric Triglyceride, Propylene Glycol, Butyloctyl Salicylate, Cyclopentasiloxane, Dimethiconol, Dimethicone Crosspolymer (and) Phenyltrimethicone Blend, Methylisothiazolinone & Phenoxyethanol, Fragrance, Cyclotetrasiloxane (and) Cyclopentasiloxane (and) Dimethicone (and) Trisiloxane (and) Phenyl trimethicone (and) Isoparaffinic hydrocarbon, Titanium dioxide, Aluminium Hydroxide, Pentaerithrityl Tetra-di-t-butyl Hydroxyhydrocinnamate, *Pterocarpus marsupium* Bark extract}, Tocopheryl Acetate, Acrylates/C10-30 Alkyl Acrylate Crosspolymer, Disodium EDTA,

TABLE 2

Skin Care Hydration Cream

Active Ingredients

Oleanoyl-KVK
*Amaranthus* extract, Niacinamide, Vitamin E, Shea butter, Olive oil, D-Panthenol
Other ingredients/Excipients Bioavailability enhancers (Piperine extract or Tetrahydropiperine (Cosmoperine ®*)), Fragrance, Thickeners (Cellulose derivatives or Acrylates Cross Polymer),

TABLE 3

Sunscreen Cream

Active Ingredients

Oleanoyl-KVK
*Galanga* extract, Vitamin E acetate
Other ingredients/Excipients

Aqua, Ethylhexyl methoxycinnamate, Octocrylene, Ethylhexyl salicylate, Butyl Methoxydibenzoylmethane, Benzophenone - 3, Cetyl Palmitate, Sorbitan Stearate and Sucrose Cocoate, Titanium dioxide and Aluminium Hydroxide and Stearic Acid, Methyl Gluceth - 20, Cetyl Alcohol, Propylene Glycol, Glyceryl Stearate and PEG 100 Stearate, Ceteareth - 20, Dicaprylyl Carbonate, Caprylic/Capric Triglyceride, Dimethicone, Cyclotetrasiloxane (and) Cyclopentasiloxane (and) Dimethicone (and) Trisiloxane (and) Phenyl trimethicone (and) Isoparaffinic hydrocarbon, Methylisothiazolinone and Phenoxyethanol, Pentaerythrityl Tetra-di-t-butyl Hydroxyhydrocinnamate, Acrylates/C10-30

TABLE 3-continued

Sunscreen Cream

Alkyl Acrylate Crosspolymer, Tocopherol Acetate, Disodium EDTA, Amino Methyl Propanol. Bioavailability enhancers (Piperine extract or Tetrahydropiperine (Cosmoperine ®)), Fragrance, Thickeners (Cellulose derivatives or Acrylates Cross Polymer),

TABLE 4

Cleanser

Active Ingredients

Oleanoyl-KVK
Tetrahydrocurcumin, licorice extract, Pterostilbene, Tetrahydropiperine, Lemon peel extract, papaya extract
Other ingredients/Excipients Aqua, Sodium cocoyl glycinate, Lauryl Glucoside, Cocamidopropyl Betaine, Steareth 21, Cetyl alcohol, *Carica papaya* (Fruit) extract, *Citrus medica limonum* (Lemon) Peel Extract, Steareth 2, PEG-150 Distearate, Propylene Glycol, Acrylates/C10-30 alkyl acrylate crosspolymer, Polysorbate 20, Fragrance, Methylisothiazolinone & Phenoxyethanol, Tocopheryl Acetate, Aminomethyl Propanol, Mica (and) CI 77891, Pentaerithrityl Tetra-di-t-butyl Hydroxyhydrocinnamate, Disodium EDTA, bioavailability enhancers (Piperine extract or Tetrahydropiperine (Cosmoperine ®*)), Fragrance, Thickeners (Cellulose derivatives or Acrylates Cross Polymer),

TABLE 5

Face Scrub

Active Ingredients

Oleanoyl-KVK
*Cocus nucifera* extract, walnut scrub, neem oil, Niacinamide, lemon peel extract, Vitamin E acetate
Other ingredients/Excipients Aqua, Glycerin, Caprylic/Capric Triglyceride, Lauryl Glucoside, Sorbitan Stearate & Sucrose Cococate, Isopropyl Myristate, Isopropyl Palmitate & Pentaerthrityl Tetraisostearate, Cetyl Palmitate, Stearic acid, Cetostearyl Alcohol, CI 77891, *Juglans Regia* (Walnut) Shell Powder, *Zea Mays* (corn) Starch, *Azadirachta Indica* (Neem) Seed Oil, Phenoxyethanol & Methylisothiazolinone, Fragrance, Acrylates/C10-30 Alkyl Acrylate Crosspolymer, Amino Methyl Propanol, Pentaerthirtyl Tetra-di-t-butyl Hydroxyhydrocinnmate, Tocopheryl Acetate, Menthol, Disodium EDTA, bioavailability enhancers (Piperine extract or Tetrahydropiperine (Cosmoperine ®*)), Fragrance, Thickeners (Cellulose derivatives or Acrylates Cross Polymer),

TABLE 6

Anti-aging serum

Active Ingredients

Oleanoyl-KVK
Tetrahydrocurcumin, *Cocos Nucifera* (Coconut) Fruit Juice, Turmeric Oil, Argan oil, Lipactive IncaInchi ®#
Other ingredients/Excipients Cationic polymers (Galsilk 700), Disodium EDTA, glycerin, Preservatives, non-ionic surfactant (Tween 20), non-ionic solubilizers and emulsifying agents (Cremophor RH 40), Bioavailability enhancers (Piperine extract or Tetrahydropiperine (Cosmoperine ®*)), Fragrance, Thickeners (Cellulose derivatives or Acrylates Cross Polymer), Barley Beta Glucans, Vitamins

TABLE 7

Anti-Aging Cleanser

| Active Ingredients |
| --- |
| Oleanoyl-KVK |
| Tetrahydrocurcumin, *Cocos Nucifera* (Coconut) Fruit Juice, Turmeric Oil, Argan oil, Lipactive IncaInchi ®# |
| Other ingredients/Excipients |
| Niacinamide, lemon peel extract, Vitamin E acetate, Bioavailability enhancers (Piperine extract or Tetrahydropiperine (Cosmoperine ®*)), Fragrance, Thickeners (Cellulose derivatives or Acrylates Cross Polymer) |

*Registered Trademark of Sabinsa Corporation
Registered Trademark of Greentech

TABLE 8

Anti-aging balancing toner

| Active Ingredients |
| --- |
| Oleanoyl-KVK |
| Tetrahydrocurcumin, *Cocos Nucifera* (Coconut) Fruit Juice, Turmeric Oil, Argan oil, Lipactive IncaInchi ®# |
| Other ingredients/Excipients |
| Tetrahydropiperine (Cosmoperine ®*)), Fragrance, Thickeners (Cellulose derivatives or Acrylates Cross Polymer) |

*Registered Trademark of Sabinsa Corporation
Registered Trademark of Greentech

TABLE 9

Anti-aging Moisturizer

| Active Ingredients |
| --- |
| Oleanoyl-KVK |
| Tetrahydrocurcumin, *Cocos Nucifera* (Coconut) Fruit Juice, Turmeric Oil, Argan oil, Lipactive IncaInchi ®# |
| Other ingredients/Excipients |
| Barley Beta Glucans, niacinamide, policosanol, *Amaranthus* extract, Avocado Butter & *Macademia* oil Tetrahydropiperine (Cosmoperine ®*)), Fragrance, Thickeners (Cellulose derivatives or Acrylates Cross Polymer) |

*Registered Trademark of Sabinsa Corporation
Registered Trademark of Greentech

TABLE 10

Anti-aging Cream

| Active Ingredients |
| --- |
| Oleanoyl-KVK |
| Coenzyme Q10, Tetrahydrocurcumin, *Boswellia serrata* extract |
| Other ingredients/Excipients |
| *Galanga* extract, D-Panthenol, Bisabolol, Tetrahydropiperine (Cosmoperine ®*)), Fragrance, Thickeners (Cellulose derivatives or Acrylates Cross Polymer), Olive Oil, Avacado Oil and Cranberry Oil |

*Registered Trademark of Sabinsa Corporation

The above formulations are merely illustrative examples; any formulation containing the above active ingredient intended for the said purpose will be considered equivalent.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention. The scope of the invention is to be interpreted only in conjunction with the appended claims.

We claim:

1. A process for preparing a compound of structure 1 with SEQ ID #1 attached to oleanolic acid comprising the steps of:
   a. Treating Boc-Lys(Cbz)-OH, wherein both the amino groups of L-Lysine is protected, with Benzyl bromide in Acetone and potassium carbonate to get Boc-Lys (Cbz)-OBzl;
   b. Hydrolyzing the Boc-Lys(Cbz)-OBzl from step (a) to obtain H-Lys(Cbz)-OBzl.HCl;
   c. Coupling the H-Lys(Cbz)-OBzl.HCl of step (b) with Boc-Val-OH in the presence of N, N'-Dicyclohexylcarbodiimide, Hydroxy benzotriazole and triethylamine to obtain Boc-Val-Lys(Cbz)-OBzl;
   d. Treating Boc-Val-Lys(Cbz)-OBzl obtained from step c) with trifluoroacetic acid to obtain H-Val-Lys(Cbz)-OBzl;
   e. Coupling H-Val-Lys(Cbz)-OBzl of step d) with Boc-Lys(Cbz)-OH in the presence of N, N'-Dicyclohexylcarbodiimide, Hydroxy benzotriazole and triethylamine to obtain Boc-Lys(Bzl)-Val-Lys (Cbz)-OBzl;
   f. Treating Boc-Lys(Bzl)-Val-Lys(Cbz)-OBzl of step e) with trifluoroacetic acid to obtain H-Lys(Bzl)-Val-Lys (Cbz)-OBzl;
   g. Coupling the H-Lys(Bzl)-Val-Lys(Cbz)-OBzl of above step with 3-O-acetyl Oleanoyl chloride (synthesized from 3-O-acetyl oleanolic acid and thionyl chloride) in the presence of triethylamine to get (3-O-Acetyl Oleanoyl)-Lys(Bzl)-Val-Lys(Cbz)-OBzl;
   h. Hydrogenating the (3-O-Acetyl Oleanoyl)-Lys(Bzl)-Val-Lys(Cbz)-OBzl of step g) in the presence of palladium and carbon catalyst in alcohol medium to get 3-O-Acetyl Oleanoyl-Lys-Val-Lys;
   i. Hydrolyzing the acetyl group using a base in alcohol medium to obtain a tripeptide of SEQ ID #1, linked to oleanolic acid,
   wherein SEQ ID #1 is K-V-K, and structure 1 is represented as below

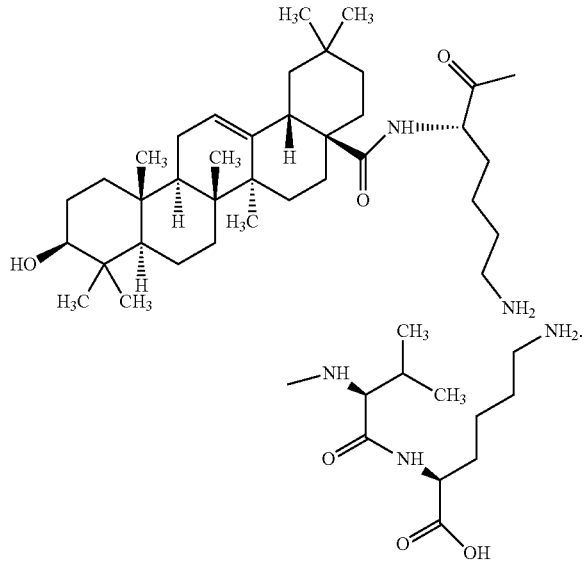

structure 1

2. The process of claim 1, wherein the base in step (i) in selected from the group consisting of sodium hydroxide, lithium hydroxide and potassium hydroxide.

3. A composition comprising a tripeptide of SEQ ID #1, linked to oleanolic acid as obtained from the process of claim 1.

4. A method of preventing skin ageing in mammals, said method comprising steps of bringing into contact mammalian skin with effective concentration of tripeptide of SEQ ID 1 linked to oleanolic acid, to prevent skin ageing.

5. The method as claimed in claim 4, wherein the symptoms of skin aging are selected from the group consisting of thinning of epidermis, decrease in melanocytes, loss of melanin production, loss of collagen and elastin, less oil production from sebaceous glands leading to loss of moisture and dryness, loss of subcutaneous fat layer, loss of insulation and padding, weak wound healing ability, sagging of skin, dryness, patchy skin, and lines.

6. The method as claimed in claim 4, wherein skin ageing is prevented by inhibiting collagenase activity.

7. The method as claimed in claim 4, wherein skin aging is prevented by inhibiting elastase activity.

8. The method as claimed in claim 4, wherein skin aging is prevented by increasing skin fibroblasts proliferation.

9. The method as claimed in claim 4, wherein skin aging is prevented by increasing collagen in skin fibroblasts.

10. The method as claimed in claim 4, wherein skin aging is prevented by enhanced secretion of TGF-$\beta$ by skin fibroblasts.

11. The method as claimed in claim 4, wherein the mammal is human.

12. The composition as claimed in claim 3, wherein the said composition is formulated with pharmaceutically/cosmeceutically acceptable excipients, adjuvants, bases, diluents, carriers, conditioning agents, bioavailability enhancers, antioxidants and preservatives and/or incorporated into formulations containing anti-aging ingredients and administered topically in the form of creams, gels, lotions, powder, serum, oil, suspensions, ointments, soaps, scrubs, emulsions, and compacts.

13. The composition as claimed in claim 3, wherein said tripeptide is present in combination with other bioactive components.

14. The composition of in claim 3, wherein the said composition acts as a skin care agent and prevents skin ageing.

15. The method as claimed in claim 4, wherein skin aging is prevented by protecting against UV-A and UV-B induced cell damage.

* * * * *